United States Patent
Johnston et al.

(10) Patent No.: US 7,205,321 B2
(45) Date of Patent: Apr. 17, 2007

(54) PEROXISOME PROLIFERATOR ACTIVATED RECEPTOR ALPHA AGONISTS

(75) Inventors: Richard Duane Johnston, Greenfield, IN (US); Nathan Bryan Mantlo, Brownsburg, IN (US); Richard Craig Thompson, Frankfort, IN (US)

(73) Assignee: Eli Lilly and Company, Indianapolis, IN (US)

( * ) Notice: Subject to any disclaimer, the term of this patent is extended or adjusted under 35 U.S.C. 154(b) by 445 days.

(21) Appl. No.: 10/495,204

(22) PCT Filed: Nov. 13, 2002

(86) PCT No.: PCT/US02/33632

§ 371 (c)(1),
(2), (4) Date: May 10, 2004

(87) PCT Pub. No.: WO03/043997

PCT Pub. Date: May 30, 2003

(65) Prior Publication Data

US 2004/0235912 A1    Nov. 25, 2004

Related U.S. Application Data

(60) Provisional application No. 60/335,818, filed on Nov. 15, 2001.

(51) Int. Cl.
*A61K 31/4245* (2006.01)
*C07D 271/10* (2006.01)

(52) U.S. Cl. ............... 514/364; 548/125; 548/143; 548/144; 514/361

(58) Field of Classification Search ............... 548/125, 548/143, 144; 514/361, 364
See application file for complete search history.

(56) References Cited

U.S. PATENT DOCUMENTS 3,971,803 A * 7/1976 Rosenberger et al. ....... 548/144

FOREIGN PATENT DOCUMENTS

| | | |
|---|---|---|
| DE | 24 22 158 A | 12/1974 |
| EP | 0 449 211 A | 10/1991 |
| WO | WO 96 13264 A | 5/1996 |
| WO | WO 97 40017 A | 10/1997 |
| WO | WO 01 17994 A | 3/2001 |
| WO | WO 01 57023 A | 8/2001 |
| WO | WO 02 38553 A | 5/2002 |
| WO | WO 02 46174 A | 6/2002 |

* cited by examiner

*Primary Examiner*—Golam M. M. Shameem
(74) *Attorney, Agent, or Firm*—MaCharri Vorndran-Jones

(57) ABSTRACT

The present invention is directed to compounds represented by the following structural formula, and pharmaceutically acceptable salts, solvates and hydrates thereof, R1 is selected from the group consisting of hydrogen, substituted or unsubstituted group selected from C1–C8 alkyl, aryl-C0-4-alkyl, heteroaryl-C0-4-alkyl, and C3–C6 cycloalkylaryl-C0-2-alkyl; W is O or S; X is an optionally substituted C1–C5 alkylene linker wherein one carbon atom of the linker may be replaced with O, NH or S; Y is C, O, S, NH or a single bond; E is C(R3)(R4)A or A

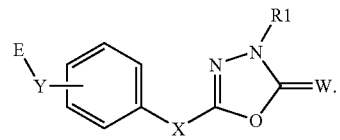

6 Claims, No Drawings

PEROXISOME PROLIFERATOR ACTIVATED RECEPTOR ALPHA AGONISTS

This Application claims the benefit of U.S. Provisional Application Ser. No. 60/335,818, filed Nov. 15, 2001, and PCT Application Serial No. PCT/US02/33632, filed Nov. 13, 2002.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, NUC1, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low-density lipoprotein (LDL) cholesterol.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). TZDs are a class of PPAR gamma agonists which have been shown to increase the sensitivity of insulin sensitive cells. Increasing insulin sensitivity rather than the amount of insulin in the blood reduces the likelihood of hypoglycemic coma. However, TZDs and ISEs typically have little effect in preventing the cardiovascular part of Syndrome X in that their administration usually dose not result in the lowering of triglycerides and LDL-cholesterol while raising HDL-cholesterol. Furthermore, side effects commonly associated with treatment with TZDs include significant weight gain, and, for troglitazone, liver toxicity. Therefore, a need exists for new pharmaceutical agents which affect treat or prevent cardiovascular disease, particularly that associated with Syndrome X, while preventing or minimizing weight gain, and more preferably while improving insulin sensitivity.

SUMMARY OF THE INVENTION

The present invention is directed to compounds represented by the following structural Formula I:

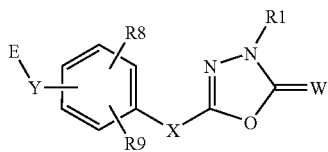

and pharmaceutically acceptable salts, solvates and hydrates thereof, wherein:
(a) R1 is selected from the group consisting of hydrogen, substituted or unsubstituted group selected from $C_1$–$C_8$ alkyl, aryl-$C_{0-4}$-alkyl, heteroaryl-$C_{0-4}$-alkyl, and C3–C6 cycloalkylaryl-$C_{0-2}$-alkyl;
(b) W is O or S;
(c) X is an optionally substituted $C_1$–$C_5$ alkylene linker wherein one carbon atom of the linker may be replaced with O, NH or S;
(d) Y is C, O, S, NH or a single bond;
(e) E is C(R3)(R4)A or A and wherein
  (i) A is an functional group selected from the group consisting of carboxyl, substituted or unsubstituted acylsulfonamide and substituted or unsubstituted tetrazole;
  (ii) R3 is H, $C_1$–$C_5$ alkyl, $C_1$–$C_5$ alkoxy, and
  (iii) R4 is H, an optionally substituted group selected from $C_1$–$C_5$ alkyl, $C_1$–$C_5$ alkoxy, $C_3$–$C_6$ cycloalkyl, aryl $C_0$–$C_4$ alkyl and phenyl, and R3 and R4 are optionally combined to form a $C_3$–$C_4$ cycloalkyl;
(f) R8 is independently selected from the group consisting of hydrogen, $C_1$–$C_4$ alkyl, $C_1$–$C_4$ alkylenyl, and halo;
(g) R9 is independently selected from the group consisting of hydrogen, $C_1$–$C_4$ alkyl, $C_1$–$C_4$ alkylenyl, halo, substituted or unsubstituted aryl, substituted or unsubstituted aryl-$C_1$–$C_4$ alkyl, substituted or unsubstituted heteroaryl, $C_1$–$C_6$ allyl, and OR10; and
(h) R10 is independently selected from the group consisting of hydrogen and $C_1$–$C_4$ alkyl.

Compounds represented by the following structural Formula I:

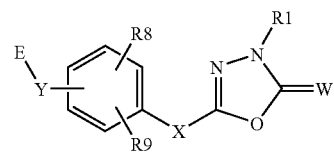

and pharmaceutically acceptable salts, solvates and hydrates thereof, wherein:
(a) R1 is selected from the group consisting of hydrogen, substituted or unsubstituted group selected from $C_1$–$C_8$ alkyl, aryl-$C_{0-4}$-alkyl, heteroaryl-$C_{0-4}$-alkyl, C3–C6 cycloalkylaryl-$C_{0-2}$-alkyl, and —$CH_2$—C(O)—R17—R18, wherein R17 is O or NH and R18 is optionally substituted benzyl;
(b) W is O or S;
(c) X is an optionally substituted $C_1$–$C_5$ alkylene linker wherein one carbon atom of the linker may be replaced with O, NH or S;
(d) Y is C, O, S, NH or a single bond; and
(e) E is selected from the group consisting of hydrogen, C(R3)(R4)A, A, substituted or unsubstituted selected from the group consisting of $(CH_2)_n$COOR19, $C_1$–$C_6$ alkyl, $C_1$–$C_6$ allyl, aryl-$C_{0-4}$-alkyl, thio-$C_{1-4}$-alkyl, thioaryl, $C_{1-4}$alkoxyaryl, $C_{1-4}$alkoxy $C_{1-4}$alkyl, aminoaryl, and amino$C_{1-4}$alkyl, and wherein
  (i) n is 0, 1, 2 or 3,
  (ii) A is an functional group selected from the group consisting of carboxyl, $C_1$–$C_3$alkylnitrile, carboxamide, substituted or unsubstituted sulfonamide, substituted or unsubstituted acylsulfonamide and substituted or unsubstituted tetrazole;
  (iii) R3 is H, $C_1$–$C_5$ alkyl, $C_1$–$C_5$ alkoxy, and
  (iv) R4 is H, halo, a substituted or unsubstituted group selected from $C_1$–$C_5$ alkyl, $C_1$–$C_5$ alkoxy, $C_3$–$C_6$ cycloalkyl, aryl $C_0$–$C_4$ alkyl and phenyl; and R3 and R4 are optionally combined to form a $C_3$–$C_4$ cycloalkyl;

(v) R19 is selected from the group consisting of hydrogen, optionally substituted C1–C4alkyl and optionally substituted arylmethyl;

(f) R8 is independently selected from the group consisting of hydrogen, $C_1$–$C_4$ alkyl, $C_1$–$C_4$ alkylenyl, and halo;

(g) R9 is independently selected from the group consisting of hydrogen, $C_1$–$C_4$ alkyl, $C_1$–$C_4$ alkylenyl, halo, substituted or unsubstituted aryl, substituted or unsubstituted aryl-$C_1$–$C_4$ alkyl, substituted or unsubstituted heteroaryl, $C_1$–$C_6$ allyl, and OR10; and R10 is independently selected from the group consisting of hydrogen and $C_1$–$C_4$ alkyl.

In another feature of this invention, a compound claimed herein is radiolabeled.

For compounds having Structural Formula I, it may be preferred that E is C(R3)(R4)A. It is generally more preferred that A is a carboxyl group. It is generally even more preferred that E is C(R3)(R4)COOH and $R_3$ $_{and\ R4}$ are each independently H or $CH_3$.

In one embodiment, the present invention also relates to pharmaceutical compositions which comprising at least one compound of the present invention, or a pharmaceutically acceptable salt, solvate, hydrate or prodrug thereof, and a pharmaceutically acceptable carrier.

In another embodiment, the present invention relates to a method of modulating a PPAR alpha receptor by contacting the receptor with at least one compound represented by Structural Formula I, and pharmaceutically acceptable salts, solvates and hydrates thereof In a further embodiment, the present invention relates to a method of making a compound represented by Structural Formula I.

The compounds of the present invention and pharmaceutically acceptable salts, solvates and hydrates thereof are believed to be effective in treating and preventing Syndrome X, Type II diabetes, hyperglycemia, hyperlipidemia, obesity, coagaulopathy, hypertension, atherosclerosis, and other disorders related to Syndrome X and cardiovascular diseases. In addition, the compounds exhibit fewer side effects than compounds currently used to treat these conditions. Further, compounds of this invention can be useful for lowering fibrinogen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, alkyl groups include straight chained or branched hydrocarbons, which are completely saturated.

As used herein, alkylene linker is an optionally unsaturated $C_1$–$C_5$ straight or branched chain hydrocarbon group. It may be preferred that alkylene linker is C1–C3 alkyl.

Cycloalkyl groups, as used herein, include cyclic hydrocarbons, which are partially or completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl).

Heterocyclic group, as used herein, is a ring system having at least one heteroatom such as nitrogen, sulfur or oxygen. Heterocyclic groups include, but are not limited to, benzofuranyl, benzothiazolyl, benzothienyl, isoquinolyl, isoxazolyl, morpholino, oxadiazolyl, pyridyl, pyrimidinyl, pyrrolyl, quinolyl, tetrahydropyranyl and thienyl.

Examples of R1, R5, E, R4, and R9 suitable substituents when said R1, E, R4, R5, or R9 are one or more independently selected from the group consisting of substituted or optionally substituted $C_1$–$C_8$alkyl, aryl, $C_1$–$C_6$ allyl, thio-$C_1$–$C_4$alkyl, thioaryl, $C_1$–$C_4$alkoxyaryl, $C_1$–$C_4$alkoxy $C_0$–$C_4$alkyl, aminoaryl and amino$C_1$–$C_4$alkyl, aryl-$C_{0-4}$ alkyl, heteroaryl$C_{0-4}$alkyl, heterocyclic, $(C_3$–$C_6)$cycloalkylaryl-$C_{0-2}$-alkyl and cycloalkyl, then suitable substituted groups include, for example, C1–C5 alkyl, C1–C5 alkoxy, C1–C5 haloalkyl, C1–C5 haloalkoxy, nitro, cyano, CHO, hydroxyl, C1–C4 alkanoic acid phenyl, aryloxy, $SO_2R7$, SR7, $SF_3$, benzyloxy, alkylcarboxamido or COOH. R7 is an alkyl or a haloalkyl. When R1, R5, E, R4, and/or R9 is substituted, it is preferred that there are from 1–3 independent substitutions on said R1, R5, E, R4, or R9 group.

Examples of suitable substituents for an "optionally substituted $C_2$–$C_5$ alkylene linker", include one or more independently selected from the group consisting of $C_1$–$C_6$ alkyl, oxo, substituted or unsubstituted aryl$C_0$–$C_3$alkyl, $C_1$–$C_3$alkoxy, hydroxy, $C_3$–$C_6$cycloalkyl and halo. When the alkylene linker is substituted, it is preferred that there are from one to three independent substitutions.

Examples of suitable substituents for a substituted or optionally substituted $C_1$–$C_3$ alkylene, include one or more independently selected from $C_1$–$C_6$alkyl, oxo, aryl $C_0$–$C_3$alkyl, $C_1$–$C_3$alkoxy, hydroxy, and halo. When the alkylene is substituted it is preferred that there are from 1–3 independent substitutions.

Examples of suitable substituents for A groups, wherein A is substituted or optionally substituted acylsulfonamide and/or tetrazole include, for example, one or more independently selected from C1–C4 alkyl, C1–C4 haloalkyl, substituted or unsubstituted heteroaryl, or substituted or unsubstituted aryl.

Suitable substitutents for R4 wherein R4 is substituted or optionally substituted $C_1$–$C_5$ alkyl, $C_1$–$C_5$alkoxy, $C_1$–$C_6$ cycloalkyl, aryl$C_0$–$C_4$alkyl or phenyl, include, for example phenyl, C1–C4 alkoxy, hydroxy and alkoxy. When R4 is substituted, it is preferred that there are from 1–4 independent substitutions on the R4 group.

As used herein the term "carboxyl" has the accepted meaning and includes, for example C(O)Oalkyl and C(O)OH.

Preferably, for the compounds of the present invention, represented by Structural Formula I, and with their respective pharmaceutical compositions, W is an oxygen.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may also exist in the form of solvates, for example hydrates, and the present invention includes each solvate and mixtures thereof.

"Pharmaceutically-acceptable salt" refers to salts of the compounds of the Structural Formula I which are substantially non-toxic to mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium and magnesium; and ammonium or substituted ammonium salts. Examples of substituted ammonium salts include, for instance, those with lower alkylamines such as trimethylamine, triethylamine; hydroxyalkylamines such as 2-hydroxyethylamine, bis-(2-hyroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydroabietylamine, glucamine, N-methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

These salts may be prepared by methods known to those skilled in the art.

Certain compounds of Structural Formula I and their salts may also exist in the form of solvates, for example hydrates, and the present invention includes each solvate and mixtures thereof.

The term, "active ingredient" means the compounds generically described by Structural Formula I as well as the salts, solvates, and prodrugs of such compounds.

The term "pharmaceutically acceptable" means that the carrier, diluent, excipients and salt must be compatible with the other ingredients of the composition, and not deleterious to the recipient thereof. Pharmaceutical compositions of the present invention are prepared by procedures known in the art using well known and readily available ingredients.

"Preventing" refers to reducing the likelihood that the recipient will incur or develop any of the pathological conditions described herein.

"Treating" refers to mediating a disease or condition and preventing, or mitigating, its further progression or ameliorate the symptoms associated with the disease or condition.

"Pharmaceutically-effective amount" means that amount of a compound, or of its salt, solvate, hydrate or prodrug thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR alpha receptor or to prevent or mediate a disease or condition. Conditions prevented or treated by PPARα receptors include diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof and/or a pharmaceutically acceptable solvate thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPARα mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, solvates and hydrates thereof, have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient, which is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixers, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substance, which may also act as flavoring agents, lubricants, solubilisers, suspending agents, binders, tablet disintegrating agents and encapsulating material.

In powders, the carrier is a finely divided solid, which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks' solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier, which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 through 8 are illustrative only and are not intended to limit the scope of the invention in any way. "Active Ingredient" refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

In yet another embodiment of the compounds of the present invention, the compound is radiolabelled, such as with carbon-14, or tritiated. Said radiolabelled or tritiated compounds are useful as reference standards for in vitro assays to identify new PPARα agonists.

SYNTHESIS

Compounds of the present invention have been formed as specifically described in the examples. Further, many compounds were prepared as more generally as shown in the following schematic. Alternative synthesis methods may also be effective and known to the skilled artisan.

14

EXEMPLIFICATION

The Examples provided herein are illustrative of the invention claimed herein and are not intended to limit the scope of the claimed invention in any way.

Exemplified Compounds

Example 1

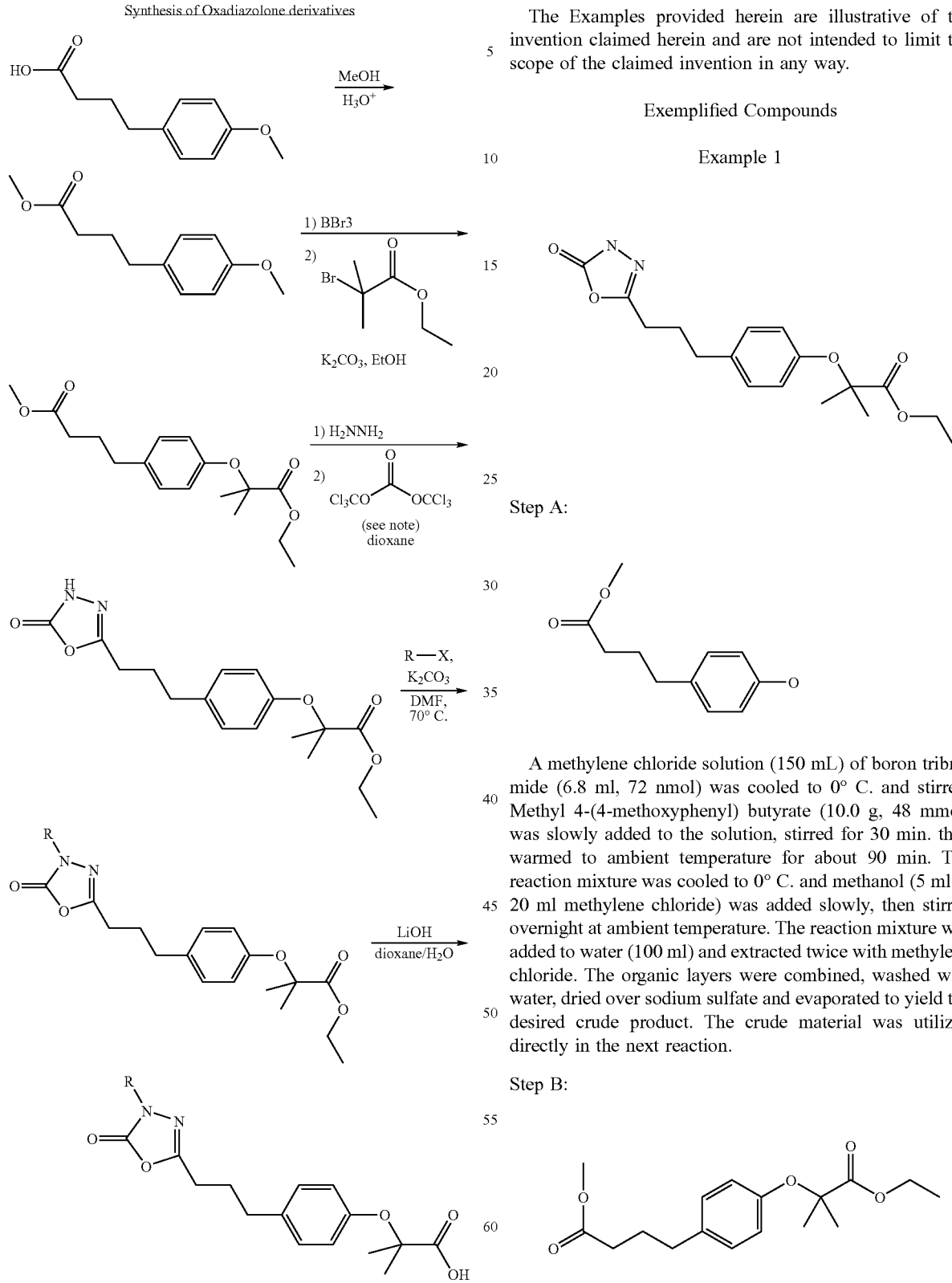

Step A:

A methylene chloride solution (150 mL) of boron tribromide (6.8 ml, 72 nmol) was cooled to 0° C. and stirred. Methyl 4-(4-methoxyphenyl) butyrate (10.0 g, 48 mmol) was slowly added to the solution, stirred for 30 min. then warmed to ambient temperature for about 90 min. The reaction mixture was cooled to 0° C. and methanol (5 ml in 20 ml methylene chloride) was added slowly, then stirred overnight at ambient temperature. The reaction mixture was added to water (100 ml) and extracted twice with methylene chloride. The organic layers were combined, washed with water, dried over sodium sulfate and evaporated to yield the desired crude product. The crude material was utilized directly in the next reaction.

Step B:

The product from Example 1, Step A (9.0 g, 46 mmol) and ethyl 2-bromoisobutyrate (13.6 ml, 93 mmol) were combined in DMF (150 ml). Potassium carbonate (powdered, 25.6 g, 186 mmol) and magnesium sulfate (5.6 g, 46 mmol)

were added and the resulting mixture stirred overnight while heating to 75° C. The reaction mixture was then added to hydrochloric acid (1N, 500 ml) which was extracted three times with ether. The combined organic layers were washed with aqueous brine then dried over sodium sulfate. Evaporation of the solvent and subsequent purification by flash chromatography (hexanes:ethyl acetate) gave the desired product.

Step C:

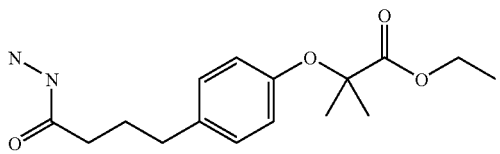

The product from Example 1, Step B (9.5 g, 31 mmol) was stirred in methanol and cooled to 0° C. Hydrazine hydrate (EM Sciences, 7.5 ml, 154 mmol) was added and the resulting solution was stirred overnight, warming to ambient temperature. The solvent was evaporated and the residue was diluted with water and extracted twice with ethyl acetate. The organic layers were combined, washed with aqueous brine and dried over sodium sulfate. Evaporation of the solvent yielded the desired product.

$C_{16}H_{24}N_2O_4$ (MW=308.4); MS: (M+1)$^+$ 309.2.

Step D:

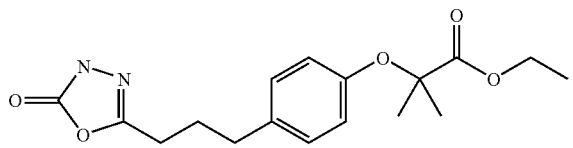

Triphosgene (1.9 g, 6.5 mmol) was dissolved in dioxane (40 ml) and cooled in an ice bath. The product from Example 1, Step C (2.0 g, 6.5 mmol, in dioxane, 10 ml) was added and stirred for 10 min, removed the ice bath and stirred at ambient temperature for 4 hours. The resulting solution was concentrated, added to water and extracted twice with ethyl acetate. The organic layers were combined and washed with aqueous brine then dried over sodium sulfate. Evaporation of the solvent and subsequent purification by flash chromatography (hexanes:ethyl acetate) yielded the product.

$C_{17}H_{22}O_5N_2$ (MW=334.4); MS: (M+1)$^+$ 335.2.

Example 2

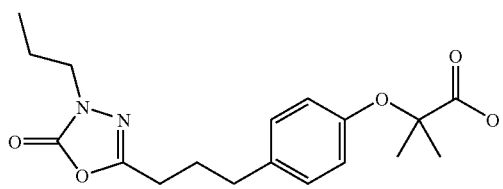

Step A:

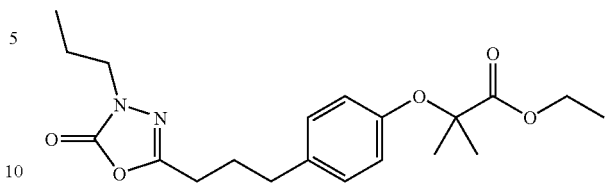

The oxadiazolone from Example 1 (0.4 g, 1.2 mmol) and iodopropane (0.23 ml, 2.4 mmol) were combined in DMF (10 ml). Potassium carbonate (powdered, 0.7 g, 4.8 mmol) and magnesium sulfate (0.14 g, 1.2 mmol) were added and the resulting mixture stirred at 75° C. for 45 minutes. The reaction mixture was added to hydrochloric acid (1N, 30 ml) which was extracted twice with ether. The combined organic layers were washed with aqueous brine then dried over sodium sulfate. Evaporation of the solvent and subsequent purification by flash chromatography (hexanes:ethyl acetate) gave the desired product.

$C_{20}H_{28}O_5N_2$ (MW=376.5); MS: (M+1)$^+$ 377.2.

Step B:

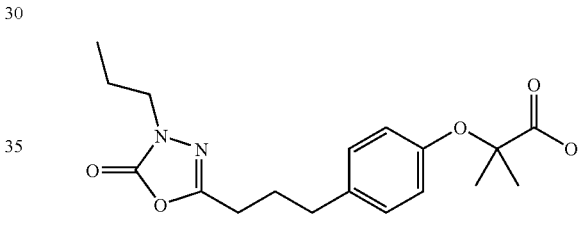

The oxadiazolone from Example 2, Step A (0.2 g, 0.53 mmol) was dissolved in dioxane (4 ml), added to lithium hydroxide (0.02 g, 0.8 mmol) dissolved in water (1 ml) and stirred at ambient temperature for 5 hours. Hydrochloric acid (5N) was added followed by water (25 ml). This was extracted three times with ethyl acetate. The organic layers were combined and dried over sodium sulfate. Evaporation of the solvent and subsequent purification by flash chromatography (ethyl acetate:hexanes) gave the desired product.

$C_{18}H_{24}O_5N_2$ (MW=348.4); MS: (M-1)$^-$ 347.2.

Example 3

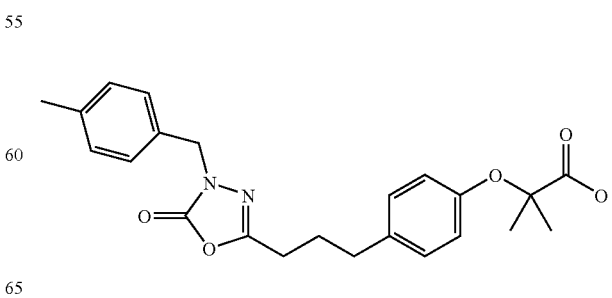

Step A:

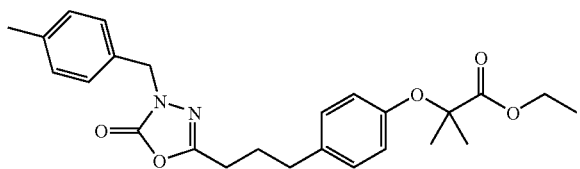

Following the procedure of Example 2, Step A, using the oxadiazolone from Example 1 (0.7 g, 2.1 mmol), α-chloro-p-xylene (0.6 g, 4.2 mmol), potassium carbonate (powdered, 1.2 g, 8.4 mmol) and magnesium sulfate (0.25 g, 2.1 mmol) the desired product was obtained.

$C_{25}H_{30}O_5N_2$ (MW=438.5); MS: $(M+1)^+$ 439.2.

Step B:

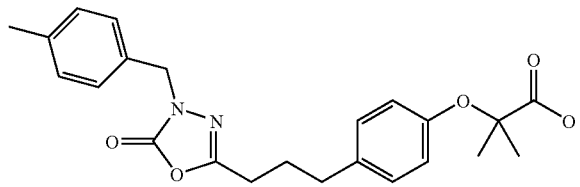

Following the procedure of Example 2, Step B, using the oxadiazolone from Example 3, Step A (0.25 g, 0.57 mmol) and 1.5 eq LiOH, the desired product was obtained after chromatographic purification.

$C_{23}H_{26}N_2O_5$ (MW=410.5); MS: $(M-1)^-$ 409.2.

Example 4

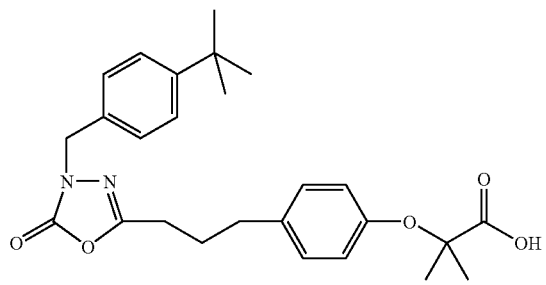

Step A:

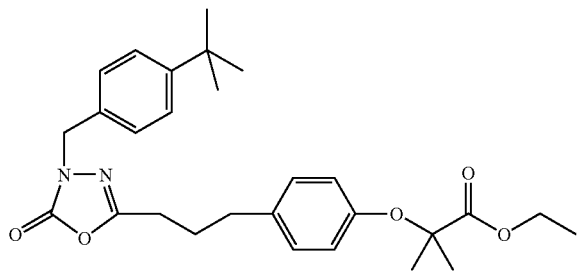

The oxadiazolone from Example 1 (0.250 g, 0.00075 mol) was dissolved in DMF (4 ml) and treated with powdered $K_2CO_3$ (0.414 g, 0.0030 mol) followed by 4-(tert-butyl)benzyl bromide (0.165 ml, 0.00090 mol). Magnesium sulfate (0.090 g, 0.00075 mol) was added to the mixture and the reaction was stirred at 75° C. for one hour. The reaction mixture was poured into 1N HCl (20 ml) and extracted with ether (3×). The organic layers were combined and concentrated to afford the desired product. The material was carried forth without further purification.

$C_{28}H_{36}N_2O_5$ (MW=480.3); MS: $(M+1)^+$ 481.2.

Step B:

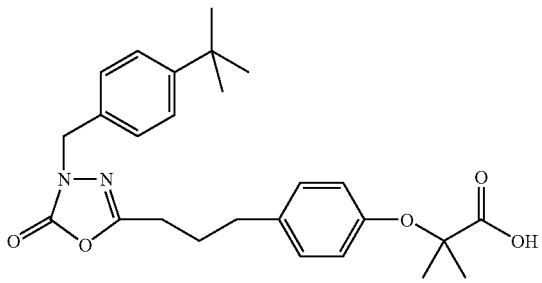

The ester from Example 4, Step A (0.350 g, 0.00072 mol) was dissolved in dioxane (7 ml) and treated with an aqueous solution of LiOH (1.4 eq). The reaction was stirred for about four hours at room temperature. The reaction mixture was acidified with 5N HCl. Water was added (25 ml) and the solution was extracted with ethyl acetate (2×). The organic layer was concentrated. Purification by flash chromatography (100% ethyl acetate) gave the acid.

$C_{26}H_{32}N_2O_5$ (MW=452.2); MS: $(M+1)^+$ 453.2.

Example 5

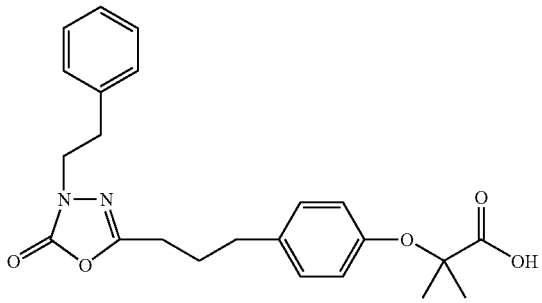

Step A:

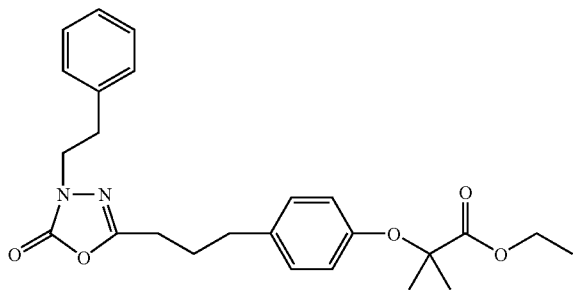

The oxadiazolone from Example 1 (0.250 g, 0.00075 mol) was dissolved in DMF (4 ml) and treated with powdered $K_2CO_3$ (0.414 g, 0.0030 mol) followed by (2-bromoethyl) benzene (0.122 ml, 0.00090 mol). Magnesium sulfate was added to the mixture and the reaction was stirred at 75° C. for one hour. The reaction mixture was poured into 1N HCl (20 ml) and extracted with ether (3×). The combined organic layers were washed with brine, dried over $Na_2SO_4$ and concentrated to afford the desired product. The material was carried forth without further purification.

Step B:

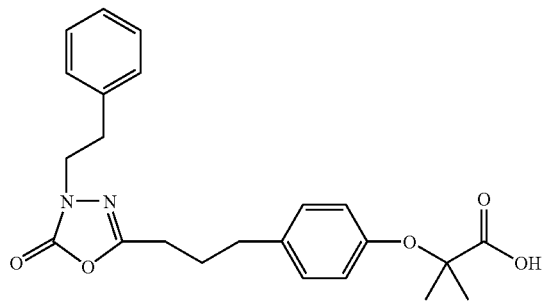

The ester from Example 5, Step A (0.400 g, 0.00090 mol) was dissolved in dioxane (7 ml) and treated with an aqueous solution of LiOH (1 eq). The reaction was stirred for three hours at room temperature. The reaction mixture was acidified with 5N HCl. Water was added (25 ml) and the solution was extracted with ethyl acetate. Purification by flash chromatography (2:1 hexanes:ethyl acetate) gave the acid.

$C_{23}H_{26}N_2O_5$ (MW=410.2); MS: $(M+1)^+$ 411.2.

Example 6

Step A:

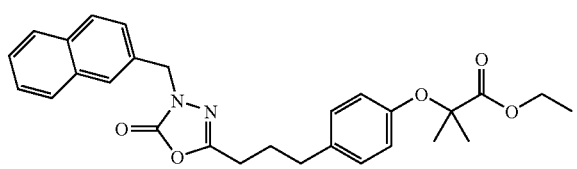

Following the procedure of Example 2, Step A, using the oxadiazolone from Example 1 (0.25 g, 0.75 mmol), 2-(bromoethyl)napthalene (0.2 g, 0.9 mmol), potassium carbonate (powdered, Aldrich, 0.41 g, 3.0 mmol) and magnesium sulfate (0.1 g, 0.8 mmol), the desired product was obtained.

$C_{28}H_{30}N_2O_5$ (MW=474.6); MS: $(M+1)^+$ 475.2.

Step B:

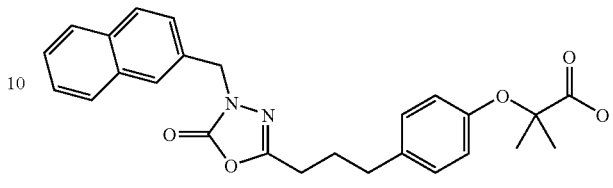

Following the procedure of Example 2, Step B, using the oxadiazolone from Example 6, Step A (0.75 mmol) and 1.6 eq LiOH, the desired product was obtained after chromatographic purification.

$C_{26}H_{26}N_2O_5$ (MW=446.5); MS: $(M-1)^-$ 445.3.

Example 7

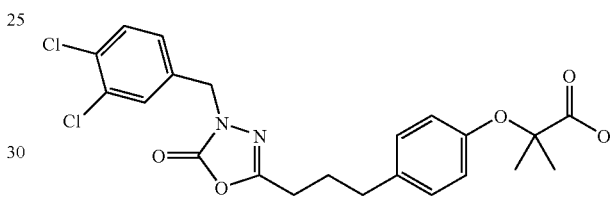

Step A:

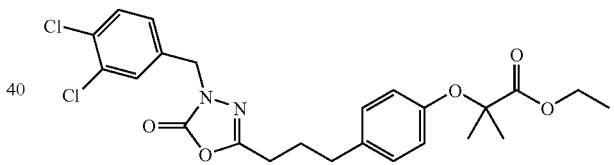

Following the procedure of Example 2, Step A, using the oxadiazolone from Example 1 (0.25 g, 0.75 mmol), 3,4-dichlorobenzyl bromide (0.22 g, 0.9 mmol), potassium carbonate (powdered, 0.41 g, 3.0 mmol) and magnesium sulfate (0.1 g, 0.8 mmol), the desired product was obtained.

$C_{24}H_{26}N_2O_5Cl_2$ (MW=493.4); MS: $(M+1)^+$ 493.1.

Step B:

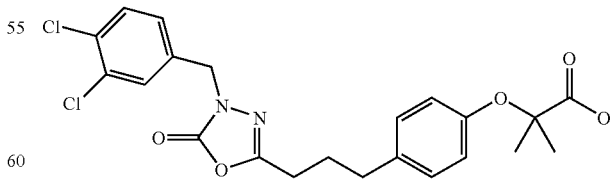

Following the procedure of Example 2, Step B, using the oxadiazolone from Example 7, Step A (0.75 mmol) and 1.6 eq LiOH, the desired product was obtained after chromatographic purification.

$C_{22}H_{22}N_2O_5Cl_2$ (MW=465.3); MS: $(M-1)^-$ 463.3.

Example 8

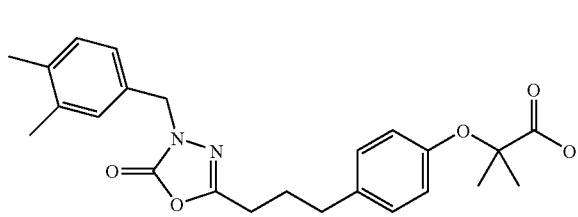

Step A:

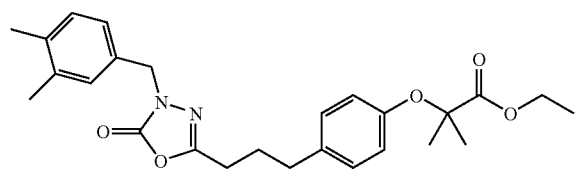

Following the procedure of Example 2, Step A, using the oxadiazolone from Example 1 (0.25 g, 0.75 mmol), 3,4-dimethylbenzyl chloride (0.14 g, 0.9 mmol), potassium carbonate (powdered, Aldrich, 0.41 g, 3.0 nmol) and magnesium sulfate (0.1 g, 0.8 mmol), the desired crude product was obtained.

Step B:

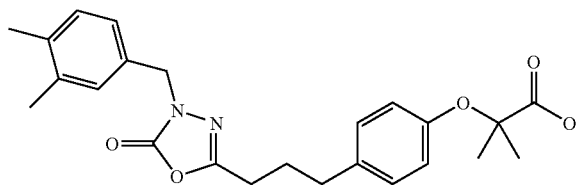

Following the procedure of Example 2, Step B, using the oxadiazolone from Example 8, Step A (0.75 mmol) and 1.6 eq LiOH, the desired product was obtained after chromatographic purification.

$C_{24}H_{28}N_2O_5$ (MW=424.5); MS: (M−1)⁻, 423.3.

Example 9

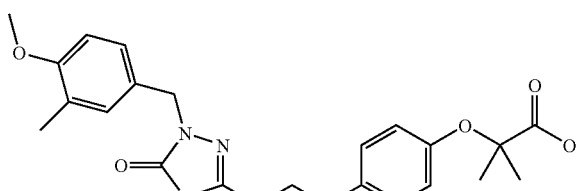

Step A:

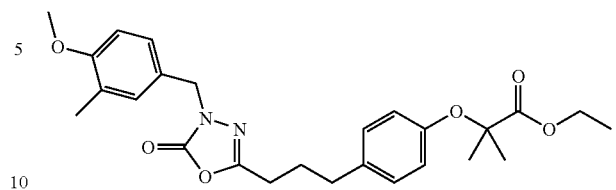

Following the procedure of Example 2, Step A, using the oxadiazolone from Example 1 (0.25 g, 0.75 mmol), 4-methoxy-3-methylbenzyl chloride (0.15 g, 0.9 mmol), potassium carbonate (powdered, 0.41 g, 3.0 mmol) and magnesium sulfate (0.1 g, 0.8 mmol), the desired crude product was obtained.

Step B:

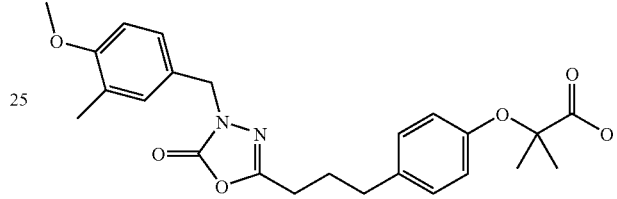

Following the procedure of Example 2, Step B, using the oxadiazolone from Example 9, Step A (0.75 mmol) and 1.6 eq LiOH, the desired product was obtained after chromatographic purification.

$C_{24}H_{28}N_2O_6$ (MW=440.5); MS: (M−1)⁻ 439.3.

Example 10

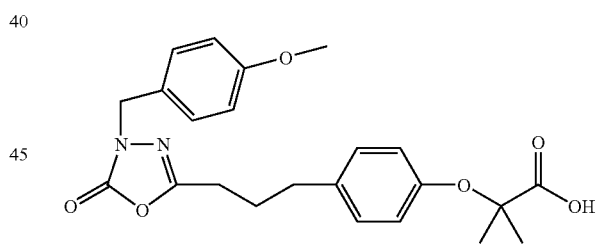

Step A:

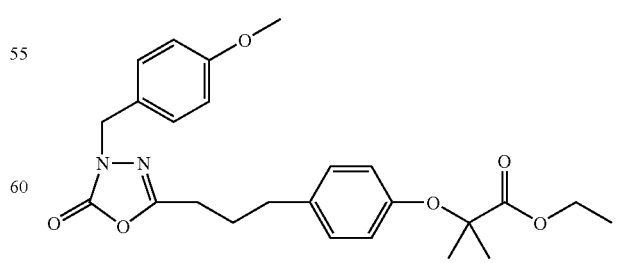

The oxadiazolone from Example 1 (0.250 g, 0.00075 mol) was dissolved in DMF (4 ml) and treated with powdered $K_2CO_3$ (0.414 g, 0.0030 mol) followed by 4-methoxybenzylchloride (0.122 ml, 0.00090 mol). Magnesium sulfate was added to the mixture and the reaction was stirred at 75° C. for one hour. The reaction mixture was poured into 1N HCl (20 ml) and extracted with ether (2×). The combined organic layers were washed with brine, dried over Na$_2$SO$_4$ and concentrated to afford the desired product (0.341 g, 100%). The material was carried forth without further purification.

Step B:

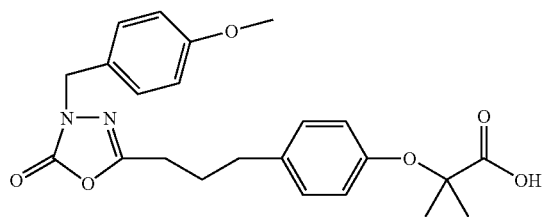

The ester from Example 10, Step A (0.341 g, 0.00075 mol) was dissolved in dioxane (7 ml) and treated with an aqueous solution of LiOH (1.5 eq). The reaction was stirred for three hours at room temperature. The reaction mixture was acidified with 5N HCl. Water was added (25 ml) and the solution was extracted with ethyl acetate. Purification by flash chromatography (2:1 hexanes:ethyl acetate) gave the acid.

C$_{23}$H$_{26}$N$_2$O$_6$ (MW=426.2); MS: (M+1)$^+$ 427.2.

Example 11

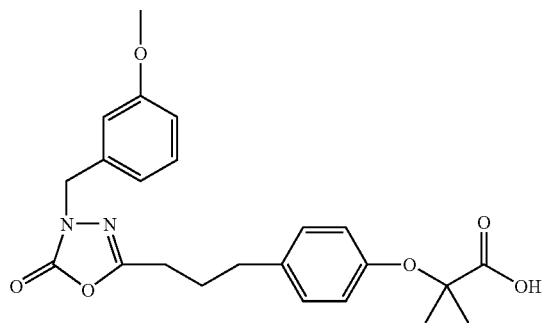

Step A:

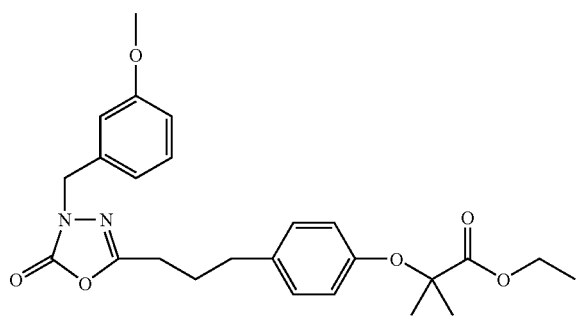

The oxadiazolone from Example 1 (0.250 g, 0.00075 mol) was dissolved in DMF (4 ml) and treated with powdered K$_2$CO$_3$ (0.414 g, 0.0030 mol) followed by 3-methoxy benzyl bromide (0.126 ml, 0.00090 mol). Magnesium sulfate was added to the mixture and the reaction was stirred at 75° C. for 45 minutes. The reaction mixture was poured into 1N HCl (20 ml) and extracted with ether (3×). The combined organic layers were washed with brine, dried over Na$_2$SO$_4$ and concentrated to afford the desired product. The material was carried forth without further purification.

Step B:

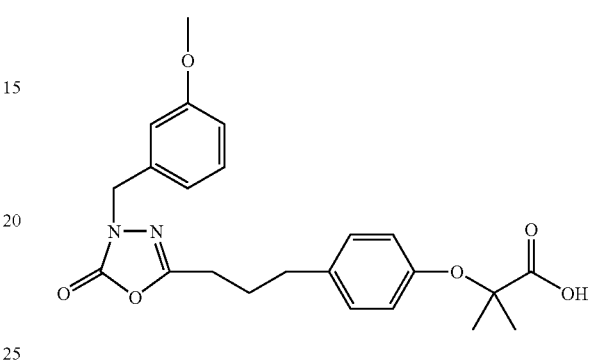

The ester from Example 11, Step A (0.275 g, 0.00060 mol) was dissolved in dioxane and treated with an aqueous solution of LiOH (1 eq). The reaction was stirred for four hours at room temperature. The reaction mixture was acidified with 5N HCl. Water was added (25 ml) and the solution was extracted with ethyl acetate (2×). The combined organic layers were concentrated. Purification by flash chromatography (2:1 hexanes:ethyl acetate) gave the acid. C$_{23}$H$_{26}$N$_2$O$_6$ (MW=426.2); MS: (M+1)$^+$ 427.2.

Example 12

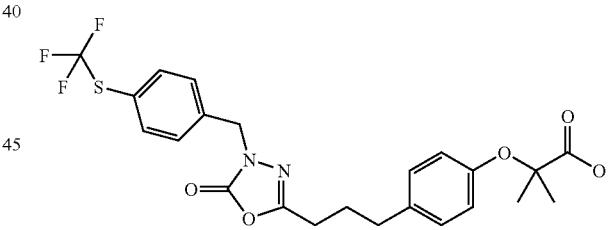

Step A:

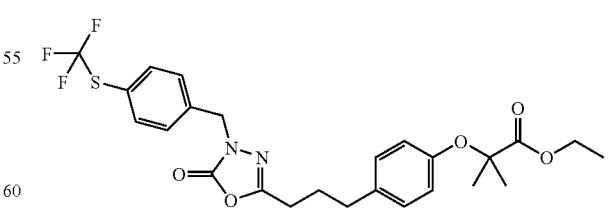

Following the procedure of Example 2, Step A, using the oxadiazolone from Example 1 (0.22 g, 0.66 nmol), 4-(trifluoromethylthio)benzyl (0.24 g, 0.9 mmol), potassium carbonate (powdered, 0.41 g, 3.0 mmol) and magnesium sulfate (0.1 g, 0.8 mmol), the desired crude product was obtained.

Step B:

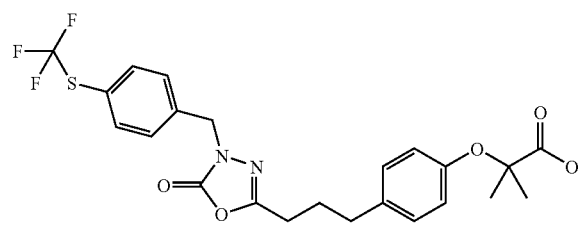

Following the procedure of Example 2, Step B, using the oxadiazolone from Example 12, Step A (0.32 g, 0.61 mmol) and 2 eq LiOH, the desired product was obtained after chromatographic purification.

$C_{23}H_{23}N_2O_5SF_3$ (MW=496.5); MS: (M−1)⁻ 495.3.

Example 13

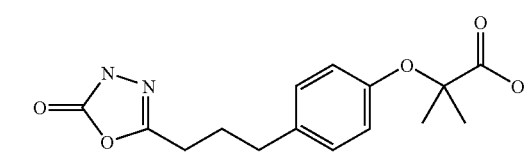

The t-butylexter of the oxadiazolone from Example 1, Step D (0.15 g, 0.4 mmol), and trifluoroacetic acid (0.05 g, 0.4 mmol) were stirred together in methylene chloride (5 ml) at ambient temperature over 2 days. The reaction was concentrated and subsequent purification by flash chromatography (hexanes:ethyl acetate) yielded the desired product.

$C_{15}H_{18}N_2O_5$ (MW=306.3); MS: (M−1)⁻ 305.1.

Example 14

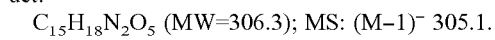

Step A:

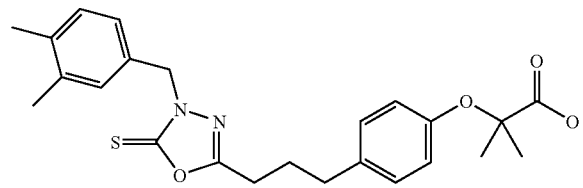

Thiophosgene (0.35 g, 3.0 mmol) was dissolved in dioxane (10 ml) and the t-butyl ester of the product from Example 1, Step C (1.0 g, 3.0 mmol, in dioxane, 5 ml) was added and stirred overnight at ambient temperature. The resulting solution was added to water and extracted twice with ether. The organic layers were combined and washed with aqueous brine then dried over sodium sulfate. Evaporation of the solvent and subsequent purification by flash chromatography (hexanes:ethyl acetate) yielded the product.

$C_{19}H_{26}O_4N_2S$ (MW=378); MS: (M−1)⁻ 377.2.

Step B:

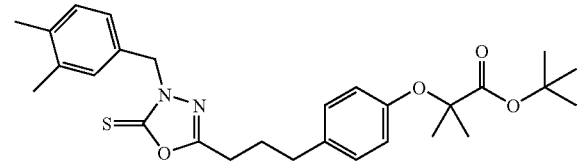

Following the procedure of Example 2, Step A, using the oxathiadiazolone from Example 14, Step A (0.25 g, 0.66 mmol), 3,4-dimethylbenzyl chloride (0.12 g, 0.79 mmol), potassium carbonate (powdered, Aldrich, 0.41 g, 3.0 mmol) and magnesium sulfate (0.1 g, 0.8 mmol), the desired crude product was obtained.

$C_{28}H_{36}N_2O_4S$ (MW=496.7); MS: (M+1)⁺ 497.2.

Step C:

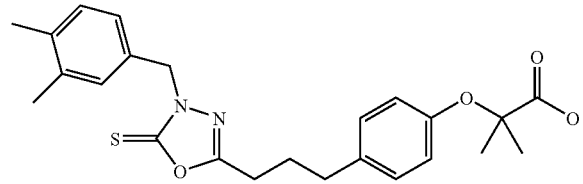

Following the procedure of Example 13, using the oxathiadiazolone from Example 14, Step B, (0.15 g, 0.3 mmol) and 2 equivalents of trifluoroacetic acid, the desired product was obtained after chromatographic purification.

$C_{24}H_{28}N_2O_4S$ (MW=440.5); MS: (M−1)⁻ 439.1.

Example 15

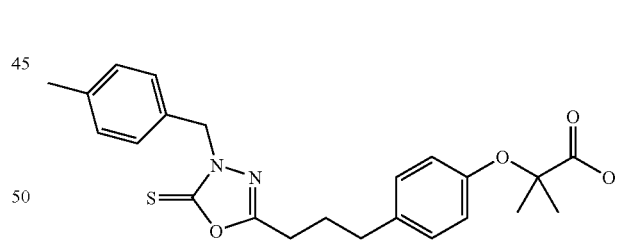

Step A:

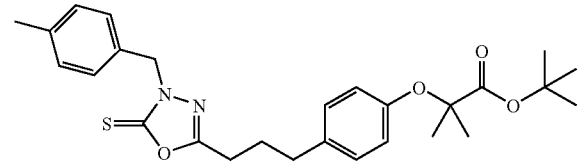

Following the procedure of Example 2, Step A, using the oxathiadiazolone from Example 14, Step A (0.25 g, 0.66 mmol), α-chloro-p-xylene (0.11 g, 0.79 mmol), potassium carbonate (powdered, 0.41 g, 3.0 mmol) and magnesium sulfate (0.1 g, 0.8 mmol), the desired crude product was obtained.

$C_{27}H_{34}N_2O_4S$ (MW=482.7); MS: $(M+1)^+$ 483.2.

Step B:

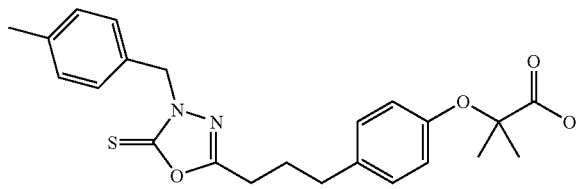

Following the procedure of Example 13, using the oxathiadiazolone from Example 15, Step A, (0.14 g, 0.3 mmol) and 2 equivalents of trifluoracetic acid, the desired product was obtained after chromatographic purification.

$C_{23}H_{26}N_2O_4S$ (MW=426.5); MS: $(M-1)^-$ 425.2.

Biological Assays

Binding and Cotransfection Studies

The in vitro potency of compounds in modulating PPARα receptors is determined by the procedures detailed below. DNA-dependent binding (ABCD binding) is carried out using SPA technology with PPAR receptors. Tritium-labeled PPARα agonists are used as radioligands for generating displacement curves and $IC_{50}$ values with compounds of the invention. Cotransfection assays are carried out in CV-1 cells. The reporter plasmid contains an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 μM).

These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values found for compounds of this invention which are useful for modulating a PPAR alpha receptor, are ≦100 nM and ≧50%, respectively.

Evaluation of Triglyceride Reduction and HDL Cholesterol Elevation in HuapoAI Transgenic Mice For each compound tested, seven to eight week old male mice, transgenic for human apoAI (C57BL/6-tgn(apoa1) 1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO2 and blood is removed (0.5–1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured calorimetrically using commercially prepared reagents (for example, as available from Sigma #339-1000 and Roche #450061 for triglycerides and cholesterol, respectively). The procedures are modified from published work (McGowan M. W. et al., Clin Chem 29:538–542,1983; Allain C. C. et al., Clin Chem 20:470–475,1974. Commercially available standards for triglycerides and total cholesterol, respectively, commercial quality control plasma, and samples are measured in duplicate using 200 μl of reagent. An additional aliquot of sample, added to a well containing 200 μl water, provides a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min is mixed with the column effluent through a T-connection and the mixture passed through a 15 m×0.5 mm id knitted tubing reactor immersed in a 37 C water bath. The colored product produced in the presence of cholesterol is monitored in the flow stream at 505 nm and the analog voltage from the monitor is converted to a digital signal for collection and analysis. The change in voltage corresponding to change in cholesterol concentration is plotted vs. time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is Compared to Mice Receiving the Vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, an increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements can reveal a significant reduction in respiratory quotient (RQ) in treated animals during the dark cycle. This reduction in RQ is indicative of an increased utilization of fat during the animals' active (dark) cycle. Additionally, treated animals displaying significantly higher rates of energy expenditure than control animals suggest a compound that may be especially desired.

Male $KK/A^y$ Mice

Male $KK/A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

The effect of administration of a Compound of this invention for 14 days is studied for the percent reduction in LDL level with reference to the vehicle group. The LDL-lowering efficacy for certain compounds of this invention is especially desirable. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired.

Method to Elucidate the Fibrinogen-Lowering Effect of PPAR Modulators

Zucker Fatty Rat Model

The life phase of the study on fibrinogen-lowering effect of compounds of this invention is part of the life phase procedures for the antidiabetic studies of the same compounds. On the last ($14^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen

Rat plasma fibrinogen levels are quantified by using a commercial assay system consisting of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound is represented by the following structural formula:

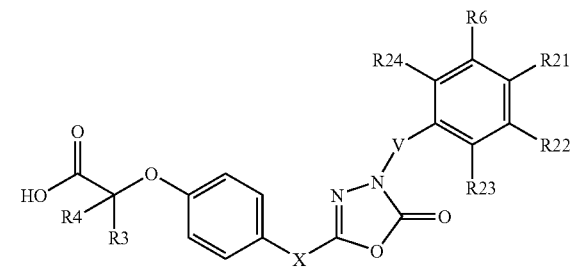

and pharmaceutically acceptable salts, solvates and hydrates thereof, wherein:
  (a) X is selected from the group consisting of an optionally substituted $C_1$–$C_3$ alkylene linker wherein one carbon atom of the linker may be replaced with O, NH or S;
  (b) R3 is selected from the group consisting of H, $C_1$–$C_5$ alkyl, and $C_1$–$C_5$ alkoxy;
  (c) R4 is selected from the group consisting of H, a substituted or unsubstituted group selected from the group consisting of $C_1$–$C_5$ alkyl, $C_1$–$C_5$ alkoxy, $C_3$–$C_6$ cycloalkyl and phenyl; and R3 and R4 are optionally combined to form a $C_3$–$C_4$ cycloalkyl;

(d) V is selected from the group consisting of a bond and a unsubstituted or substituted C1–C3 alkylene group; and (e) R6, R21, R22, R23 and R23 are each independently selected from the group consisting of H, OH, C1–C5 alkyl, alkoxy, halo, haloalkyl, haloalkoxy, nitro, phenyl, aryloxy, SO2R7, SR7, cyano, benzyloxy, phenoxy, alkylcarboxamido; or COOH wherein R7 is an alkyl or a haloalkyl.

2. A compound of claim 1 wherein V is methylene.

3. A compound is represented by the following structural formula:

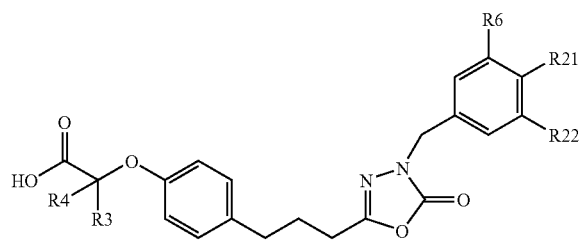

and pharmaceutically acceptable salts, solvates and hydrates thereof, wherein:

(a) R3 is selected from the group consisting of H, $C_1$–$C_5$ alkyl, and $C_1$–$C_5$ alkoxy;

(b) R4 is selected from the group consisting of H, a substituted or unsubstituted group selected from $C_1$–$C_5$ alkyl, $C_1$–$C_5$ alkoxy, $C_3$–$C_6$ cycloalkyl and phenyl; and R3 and R4 are optionally combined to form a $C_3$–$C_4$ cycloalkyl; and (c) R6, R21, and R22 are each independently selected from the group consisting of H, OH, C1–C5 alkyl, alkoxy, halo, haloalkyl, haloalkoxy, nitro, phenyl, aryloxy, SO2R7, SR7, cyano, benzyloxy, phenoxy, alkylcarboxamido and COOH wherein R7 is an alkyl or a haloalkyl.

4. A method of treating diabetes mellitus in a mammal, comprising the step of administering to the mammal a therapeutically effective amount of at least one compound of claim 1, or a pharmaceutically acceptable salt, solvate or hydrate thereof.

5. A method of treating Syndrome X in a mammal, comprising the step of administering to the mammal a therapeutically effective amount of at least one compound of claim 1, or a pharmaceutically acceptable salt, solvate or hydrate thereof.

6. A method for treating cardiovascular disease in a mammal in need thereof, comprising the step of administering to the mammal a therapeutically effective amount of at least one compound of claims 1, or a pharmaceutically acceptable salt, solvate or hydrate thereof.

* * * * *